United States Patent
Oberhauser

Patent Number: 5,919,939
Date of Patent: Jul. 6, 1999

[54] PREPARATION OF CEPHEM AND ISOOXACEPHEM DERIVATIVES

[75] Inventor: Thomas Oberhauser, Riehen, Switzerland

[73] Assignee: Hoffmann-La Roche Inc., Nutley, N.J.

[21] Appl. No.: 09/081,759

[22] Filed: May 20, 1998

Related U.S. Application Data

[62] Division of application No. 08/856,070, May 14, 1997, Pat. No. 5,883,247.

[51] Int. Cl.[6] ............ C07D 501/04; C07D 507/08; C07F 9/165
[52] U.S. Cl. ........................................... 548/119
[58] Field of Search .................................. 548/119

[56] References Cited

U.S. PATENT DOCUMENTS

| | | | |
|---|---|---|---|
| 3,971,778 | 7/1976 | Cook et al. | 260/243 C |
| 4,263,432 | 4/1981 | Iwanami et al. | 544/21 |
| 4,399,131 | 8/1983 | Dürckheimer et al. | 544/23 |
| 4,404,373 | 9/1983 | Iwanami et al. | 544/21 |
| 4,409,214 | 10/1983 | Takaya et al. | 544/22 |
| 4,576,749 | 3/1986 | Zahler | 540/362 |
| 5,523,400 | 6/1996 | Wei et al. | 540/222 |

FOREIGN PATENT DOCUMENTS

| | | |
|---|---|---|
| 0 620 225 | 10/1994 | European Pat. Off. . |
| 0620228 | 10/1994 | European Pat. Off. . |
| 2824559 | 1/1979 | Germany . |
| 2857816 | 1/1979 | Germany . |
| 96/12712 | 5/1996 | WIPO . |
| WO 96/26943 | 9/1996 | WIPO . |
| 97/24358 | 7/1997 | WIPO . |

OTHER PUBLICATIONS

Kamachi, et al. Improved Synthesis of an Ester–Type Prodrug, 1–Acetoxyethyl 7–[(Z)–2–(2–Aminothiazol–4–YL)–2–Hydroxyiminoacetamido]–3–[(Z)–1–Propenyl]–3–Cephem–4–Carboxylate (BMY–28271), The Journal of Antibiotics, vol. 43, pp. 1564–1572 (1990).
English language Abstract for DE 2824 559 (1979).
English language Abstract for DE 2857 816 (1979).

*Primary Examiner*—Mark L. Berch
*Attorney, Agent, or Firm*—George W. Johnston; William H. Epstein; Lewis J. Kreisler

[57] ABSTRACT

The invention is concerned with a new process for the preparation of compounds of formula

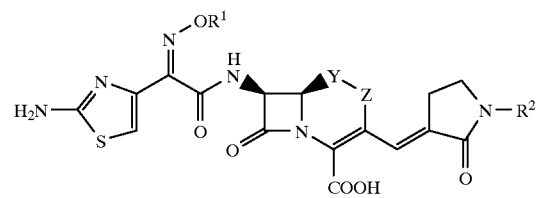

wherein
$R^1$ is trityl, acetyl, tetrahydropyranyl or cyclopentyl;
$R^2$ is hydrogen, hydroxy, lower alkyl, cycloalkyl, lower alkoxy, lower alkenyl, lower alkynyl, aryl, aryloxy, aryl-lower alkyl, aryl-lower alkoxy or heterocyclyl or heterocyclyl-lower alkyl; the lower alkyl, cycloalkyl, lower alkoxy, lower alkenyl, cycloalkenyl, lower alkynyl, aryl-lower alkyl, aryl, aryloxy, aryl-lower alkoxy, the heterocyclyl moieties being unsubstituted or substituted with at least one group selected from carboxy, amino, nitro, cyano, lower alkyl, lower alkoxy, hydroxy, halogen, —$CONR^{21}R^{22}$, —$N(R^{22})COOR^{23}$, $R^{22}CO$—, $R^{22}OCO$— or $R^{22}COO$—, wherein $R^{21}$ is hydrogen, lower alkyl, or cycloalkyl; $R^{22}$ is hydrogen or lower alkyl; $R^{23}$ is lower alkyl, lower alkenyl or a carboxylic acid protecting group;
Y is —S— and Z is —$CH_2$— or
Y is —$CH_2$— and Z is —O—,
by acylation of a compound of formula

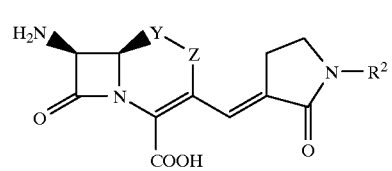

with an activated carboxylic acid derivative of formula

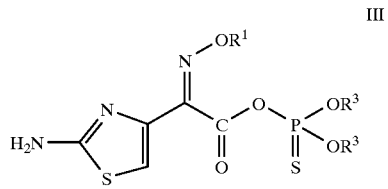

wherein $R^3$ is lower alkyl, and $R^1$, $R^2$, X, Y, Z have the significance given above; and it is further concerned with compounds of formula III.

4 Claims, No Drawings

PREPARATION OF CEPHEM AND ISOOXACEPHEM DERIVATIVES

This is a divisional of U.S. Ser. No. 08/856,070, filed May 14, 1997 now U.S. Pat. No. 5,883,247.

FIELD OF THE INVENTION

This invention relates to a process for preparing cephem and isooxacephem cephalosporin derivatives, and intermediates therefor.

BACKGROUND OF THE INVENTION

U.S. Pat. No. 5,523,400, issued Jun. 4, 1996 (Wei, et al) discloses certain cephalosporin antibiotics having a lactam moiety at the 3 position of the cephalosporin.

U.S. Pat. No. 4,409,214, issued Oct. 11, 1983 (Takaya, et al) discloses 7-acylamino-3-vinyl-cephalosporanic acid derivatives having antimicrobial activity.

Kamachi, et al, *J. Antibiotics* (December 1990) Vol. 43, pages 1564–1572 discloses the synthesis of 1-Acetoxyethyl 7-[(Z)-2-(2-aminothiazol4-yl)-2-hydroxyiminoacetamido]-3-[(Z)-1-propenyl]-3-cephem4-carboxylate by acylation of the cephem unit with an activated aminothiazole derivative in which the activating group is a benzothiazolyl ester.

European Patent Publication No. EP 620228, published Oct. 19, 1994 (Lucky, Ltd.) discloses thiophosphate derivatives of thia(dia)zole acetic acid for use in the preparation of β-lactam antibiotics. In this case the cephem unit is acylated using an activated aminothiazole derivative in which the activating group is a mixed anhydride of thiophosphoric acid.

Other acyl groups which can be used to acylate β-lactam antibiotics may be found in Cephalosporins and Penicillins, Flynn, ed, Academic Press (1972); Belgian Patent No. 866,038, published Oct. 17, 1978; Belgian Patent No. 867, 994, published Dec. 11, 1978; and U.S. Pat. No. 3,971,778, issued Jul. 27, 1976.

SUMMARY OF THE INVENTION

The present invention is concerned with a process for the preparation of cephem- and isooxacephem derivatives of formula

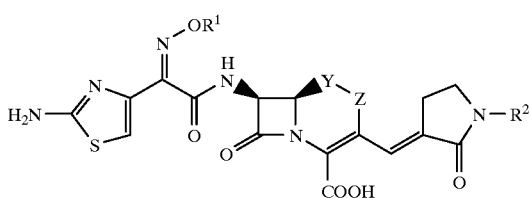

wherein
$R^1$ is trityl, acetyl, tetrahydropyranyl or cyclopentyl;
$R^2$ is hydrogen, hydroxy, lower alkyl, cycloalkyl, lower alkoxy, lower alkenyl, lower alkynyl, aryl, aryloxy, aryl-lower alkyl, aryl-lower alkoxy or heterocyclyl or heterocyclyl-lower alkyl; the lower alkyl, cycloalkyl, lower alkoxy, lower alkenyl, cycloalkenyl, lower alkynyl, aryl-lower alkyl, aryl, aryloxy, aryl-lower alkoxy, the heterocyclyl moieties being unsubstituted or substituted with at least one group selected from carboxy, amino, nitro, cyano, lower alkyl, lower alkoxy, hydroxy, halogen, —$CONR^{21}R^{22}$, —$N(R^{22})$ $COOR^{23}$, $R^{22}CO$—, $R^{22}OCO$— or $R^{22}COO$—, wherein $R^{21}$ is hydrogen, lower alkyl, or cycloalkyl; $R^{22}$ is hydrogen or lower alkyl; $R^{23}$ is lower alkyl, lower alkenyl or a carboxylic acid protecting group;
Y is —S— and Z is —$CH_2$— or
Y is —$CH_2$— and Z is —O—,
by acylation of a compound of formula

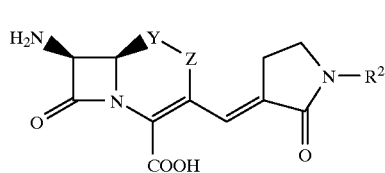

with an activated carboxylic acid derivative of formula

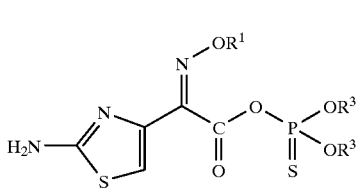

wherein $R^3$ is lower alkyl, and $R^1$, $R^2$, Y, Z have the significance given above.

The compounds of formula I are useful as antibiotics having potent and broad antibacterial activity.

This invention provides compounds of formula III.

As used herein, the term "lower alkyl" refers to both straight and branched chain saturated hydrocarbon groups having 1 to 8, preferably 1 to 4 carbon atoms, for example, methyl, ethyl, n-propyl, isopropyl, tertiary butyl and the like.

By the term "cycloalkyl" is meant a 3–7 membered saturated carbocyclic ring e.g., cyclopropyl, cyclobutyl, cyclopentyl, cyclohexyl and the like.

The term "lower alkoxy" refers to an oxygen radical having an alkyl group as defined above, examples include methoxy, ethoxy, n-propyloxy and the like.

As used herein, "lower alkenyl" refers to an unsubstituted or substituted hydrocarbon chain radical having from 2 to 8 carbon atoms, preferably from 2 to 4 carbon atoms, and having at least one olefinic double bond, e.g. vinyl, allyl and the like.

As used herein, "lower alkynyl" refers to an unsubstituted or substituted hydrocarbon chain radical having from 2 to 8 carbon atoms, preferably 2 to 4 carbon atoms, and having at least one triple bond.

The term "halogen" used herein refers to all four forms, that is chlorine or chloro; bromine or bromo; iodine or iodo; and fluorine or fluoro.

By the term "aryl" is meant a radical derived from an aromatic hydrocarbon by the elimination of one atom of hydrogen and can be substituted or unsubstituted. The aromatic hydrocarbon can be mononuclear or polynuclear. Examples of aryl radicals of the mononuclear type include phenyl, tolyl, xylyl, mesityl, cumenyl, and the like. Examples of aryl radicals of the potynuclear type include naphthyl, anthryl, phenanthryl, and the like. The aryl group can have at least one substituent selected from, as for example, halogen, hydroxy, cyano, carboxy, carbamoyl, nitro, amino, aminomethyl, lower alkyl, lower alkoxy or trifluormethyl. Examples include 2-fluorophenyl, 3-nitrophenyl, 4-nitrophenyl, 4-methoxyphenyl, 4-hydroxyphenyl and the like.

By the term "aryl-lower alkyl" is meant a lower alkyl group containing an aryl group as defined above, for example benzyl.

As used herein, "aryloxy" is an oxygen radical having an aryl substituent as defined above (i.e., —O-aryl).

As used herein, "aryl-lower alkoxy" is an oxygen radical having an aryl-lower alkyl substituent. (i.e., —O-lower-alkyl-aryl).

As used herein, "heterocyclyl ring" refers to the residue of an unsaturated or saturated, unsubstituted or substituted 5-, 6-, or 7-membered heterocyclic ring containing at least one hetero atom selected from the group consisting of oxygen, nitrogen, or sulfur. Exemplary heterocyclyl groups include, but are not limited to, e.g., the following groups: pyridyl, pyridiniumyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, thienyl, furyl, hexamethyleneiminyl, oxepanyl, 1H-azepinyl, thiophenyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, tetrahydrothienyl, and others. Substituents for the heterocyclic ring include lower-alkyl, lower-alkoxy, halogen, trifluoromethyl, trichloroethyl, amino, mercapto, hydroxy, carboxy or carbamoyl. Preferred examples of substituted heterocyclyl groups are mono-substituted and include 5-methyl-isoxazol-3-yl, N-methyl-pyridinium-2yl, 1-methyl-tetrazolyl and the like.

As used herein, "heterocyclyl-lower alkyl" refers to a lower alkyl group containing a heterocyclic group as defined above, e.g. tetrazolyl-methyl, tetrahydrofuranyl-methyl, thiophenyl-methyl or benzimidazolyl-methyl.

The heterocyclic ring can also be substituted by an optionally substituted phenyl ring such as 2,6-dichlorophenyl. Preferred is 2,6-dichlorophenyl-5-methyl-isoxazolyl.

A further substituent of the heterocyclic ring is oxo, such as in 2-oxo-oxazolidin-3-yl, 1,1-dioxo-tetrahydrothien-3-yl.

The heterocyclic ring can also be fused together with a benzene ring.

By the term "substituted phenyl" is meant phenyl mono or di-substituted.

The term "carboxylic acid protecting group" refers to protecting groups conventionally used to replace the acidic proton of a carboxylic acid. Examples of such groups are described in Greene, T., Protective Groups in Organic Synthesis, Chapter 5, pp. 152–192 (John Wiley and Sons, Inc. 1981), incorporated herein by reference. These examples include methoxymethyl, methylthiomethyl, tetrahydropyranyl, tetrahydrofuranyl, methoxyethoxymethyl, benzyloxymethyl, phenacyl, p-bromophenacyl, α-methylphenacyl, p-methoxyphenacyl, diacylmethyl, N-phthalimidomethyl, ethyl, 2,2,2-trichloroethyl, 2-haloethyl, ω-chloroalkyl, 2-(trimethylsilyl)ethyl, 2-methylthioethyl, 2-(p-nitrophenyl-sulfenyl)ethyl, 2-(p-toluenesulfonyl)ethyl, 1-methyl-1-phenylethyl, t-butyl, cyclopentyl, cyclohexyl, allyl, cinnamyl, phenyl, p-methylthiophenyl, benzyl, triphenylmethyl, diphenylmethyl, bis(o-nitrophenyl)methyl, 9-anthrylmethyl, 2-(9,10-dioxo)anthrylmethyl, 5-dibenzosuberyl, 2,4,6-trimethylbenzyl, p-bromobenzyl, o-nitrobenzyl, p-nitrobenzyl, p-methoxybenzyl, piperonyl, 4-picolyl, trimethylsilyl, triethylsilyl, t-butyldimethylsilyl, i-propyl-dimethylsilyl, phenyldimethylsilyl, S-t-butyl, S-phenyl, S-2-pyridyl, N-hydroxypiperidinyl, N-hydroxysuccinimidoyl, N-hydroxyphthalimidoyl, N-hydroxybenzo-triazolyl, O-acyl oximes, 2,4-dinitrophenylsulfenyl, 2-alkyl-1,3-oxazolines, 4-alkyl-5-oxo-1,3-oxazolidines, 5-alkyl-4-oxo-1,3-dioxolanes, triethylstannyl, tri-n-butylstannyl; the amides or hydrazides of N,N-dimethylaminio, pyrrolidinyl, piperidinyl, o-nitrophenyl, 7-nitroindolyl, 8-nitrotetrahydroquinolyl, p-benzenesulfonamide, hydrazides, N-phenylhydrazide, N,N'-diisopropylhydrazide. Preferred are benzhydryl, t-butyl, p-nitrobenzyl, p-methoxybenzyl and allyl.

DETAILED DESCRIPTION OF THE INVENTION

The process according to the invention is especially suited for the preparation of cephem and isooxacephem derivatives respectively of formula I wherein $R^1$ is hydrogen, i.e. with an hydroxyimino group, which has to be protected during the acylation step. It is essential that the protecting groups are cheap, easily removeable, recycleable and that no additional purification steps are involved due to contamination of a catalyst used during the protecting and deprotecting process. Furthermore the protecting group should not interfer with the acylation step.

It has been found that the acylation process according to invention is especially suited for the acylation of cephem- and isooxacephem derivatives of formula II with an aminothiazol derivative of formula III which is activated as mixed anhydride of thiophosphoric acid and $R^1$ is protected by a trityl, acetyl or tetrahydropyranyl group, preferably a trityl group. The yield of this reaction as well as the purity of the product are excellent and the protecting groups are easily removed to yield hydroxyimino compounds, i.e. compounds of formula I wherein $R^1$ is hydrogen.

The acylation of a compound of formula II with the activated compound of formula III is preferably carried out in a polar solvent as dimethyl formamide (DMF), dichloromethane, or a mixture of DMF/i-pronanol/water in presence of a base as e.g. triethylamine, at a temperature of about –10° C. to about 60°, preferably from about 0° C. to about 30° C.

The compounds of formula III are part of the present invention. They can be prepared as follows.

To obtain (Z)-(2-aminothiazol-4-yl)-trityl (or acetoxy, tetrahydropyranyl or cyclopentyl)oxyimino acetic acid, their precursor the unprotected (Z)-(2-aminothiazol-4-yl) oxyimino acetic acid ethylester (compound A), is commercially available. This compound is then protected as follows:

a) For the preparation of the trityl derivative (as used in example 1) the compound A is deprotonated and treated with tritylchloride to form (Z)-2-(aminothiazol4-yl) trityl-oxyimino acetic acid ethylester which is then hydrolysed to yield the free acid.

b) For the preparation of the acetyl derivative (as used in example 2) compound A is hydrolysed to form the free acid (Z)-2-(aminothiazol4-yl)oxyimino acetic acid and subsequently treated with acetanhydride in the presence of potassium carbonate to form the acetyl derivative.

c) The tetrahydropyranyl derivative (as used in Example 3) is prepared by treating the glyoxylic acid derivative described below with O-(tetrahydro-pyran-2-yl)-hydroxyl-amine in the presence of triethylamine in ethanol as depicted below:

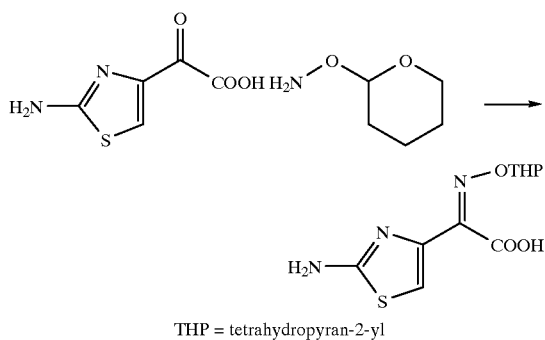

THP = tetrahydropyran-2-yl d) For the preparation of the cyclopentyl derivative the compound A is deprotonated and treated with cyclopentylbromide to form (Z)-2-(aminothiazol-4-yl) cyclopentyl-oxyimino acetic acid ethylester which is then hydrolysed to yield the free acid. The free acid is then reacted in analogy to example 1 to yield the activated acid.

The compounds of formula III are prepared by reaction of (Z)-(2-aminothiazol4-yl)-trityl (or acetoxy, or tetrahydropyranyl, or cyclopentyl) oxyimino acetic acid with di-lower alkylchloro thio phosphate in an organic solvent in the presence of a tert. amine. The compounds of formula m precipitate directly from the reaction mixture. Preferred tert. amine compounds are DABCO, tributylamine and mixtures thereof. The organic solvent is preferably dichloromethane or dimethylacetamide.

Compounds of formula II in which Y is S may be obtained from 3-cephem aldehyde as described in U.S. Pat. No. 5,523,400, issued Jun. 4, 1996 (Wei et al).

Compounds of formula II in which Z is O may be obtained from 3-isooxacephem aldehyde as shown in Scheme 1.

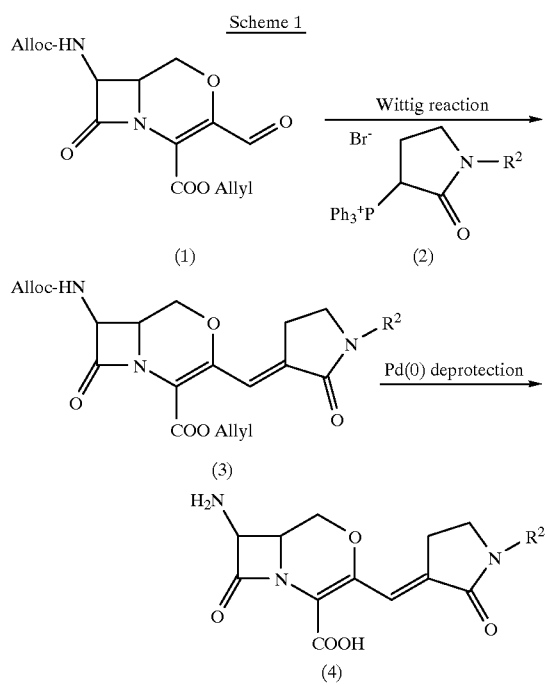

SCHEME 1

Wittig Reaction 1 to 3

The reaction of known 3-isooxacephem aldehyde (1) wherein the 7-amino-protecting group is allyloxycarbonyl and the carboxy protecting group is allyl with a Wittig reagent (2) yields the coupling product (3). The reaction is carried out in the presence of a base which is either an inorganic base (sodium or potassium hydroxide, sodium or potassium carbonate etc.), an organic base (tertiary amines), an organolithium compound such as butyl lithium or phenyl lithium or an epoxide such as 1,2-butyleneoxide. The preferred solvents are in the case of inorganic base being used, water and water-miscible solvents (acetone, tetrahydroftiran, or alcohols etc.); in the case of organic base being used, an inert solvent such as methylene chloride, chloroform, benzene, tetrahydrofuran; in the case of organolithium being used, benzene or tetrahydrofuran, and in the case an epoxide being used, the epoxide itself (e.g. 1,2-butyleneoxide). The temperature for the reaction ranges from −20° C. to 80° C.

In the normal Wittig Reaction according to scheme 1, the E isomer is the predominant product. Invariably, less than 10% Z-isomer is formed, the amount depending on the reagents and conditions.

The making of the Wittig reagent (2) can be carried out in a manner known per se; for example, by cyclization of a N-substituted dibromide using a catalyst like Dowex as described in the European Patent Application EPA 0 620 255.

Deprotection 3 to 4

The carboxylic acid protecting group $R^h$ and the amino protecting group $R^f$ are removed and the reaction conditions used are depending on the nature of the protecting groups.

In the case of the amino protecting group being allyloxycarbonyl and the carboxy protecting group being the allyl ester, Pd(0) generated in situ is employed. In the case of the amino protecting group being t-butoxycarbonyl and the carboxy protecting group being benzhydryl, trifluoroacetic acid is employed, at temperature of about −20° C. to about room temperature.

Conventional carboxylic acid protecting groups and amino protecting groups are described in Greene, T., Protective Groups in Organic Synthesis, Chapter 5, pp. 152–192 (John Wiley and Sons, Inc. 1981).

The products in accordance with the invention can be used as medicaments, for example, in the form of pharmaceutical preparations for enteral (oral) administration. The products in accordance with the invention can be administered, for example, perorally, such as in the form of tablets, coated tablets, dragees, hard and soft gelatine capsules, solutions, emulsions or suspensions, or rectally, such as in the form of suppositories.

Pharmaceutical compositions containing these compounds can be prepared using conventional procedures familiar to those skilled in the art, such as by combining the ingredients into a dosage form together with suitable, nontoxic, inert, therapeutically compatible solid or liquid carrier materials and, if desired, the usual pharmaceutical adjuvants.

It is contemplated that the compounds are ultimately embodied into compositions of suitable oral or parenteral dosage forms. The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as coprecipitated aluminum hydroxide-calcium carbonate, dicalcium phosphate or lactose; disintegrating agents, such as maize starch; and lubricating agents, such as talc. calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, coated tablets, dragees and hard gelatine capsules there can be used, for example, lactose, maize starch or derivatives thereof, talc, stearic acid or its salts. Suitable carriers for soft gelatine capsules are, for example, vegetable oils, waxes, fats and semi-solid and liquid polyols (depending on the nature of the active substance; no carriers are, however, required in the case of soft gelatine capsules). Suitable carrier materials for the preparation of solutions and syrups are, for example, water, polyols, saccharose, invert sugar and glucose. Suitable carrier materials for suppositiories are, for example, natural or hardened oils, waxes, fats and semi-liquid or liquid polyols.

As pharmaceutical adjuvants there are contemplated the usual preservatives, solubilizers, stabilizers, wetting agents, emulisifiers, sweeteners, colorants, flavorants, salts for varying the osmotic pressure, buffers, coating agents and antioxidants.

The compounds of formula I and their salts, or hydrates, can preferably be used for parenteral administration, and for this purpose are preferably made into preparations as lyophilisates or dry powders for dilution with customary agents, such as water or isotonic common salt solution.

Depending on the nature of the pharmacologically active compound the pharmaceutical preparations can contain the compound for the prevention and treatment of infectious diseases in mammals, human and non-human, a daily dosage of about 10 mg to about 4000 mg, especially about 50 mg to about 3000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 50 mg, 100 mg, 250 mg, 500 mg, 1000 mg, and 2000 mg can be contemplated.

The following examples illustrate the invention in more detail and are not intented to be a limitation in any manner.

The following abbreviations were used:
mp melting point
HPLC high performance liquid chromatography
  HPLC-analysis were performed as follows:
Sample preparation: The heterogeneous reaction mixture was dissolved with a little DMSO and diluted with $CH_3CN$.
Instrument: HP-1050 HPLC System.
Column: Machery-Nagel Nucleosil 100-5 C18 AB, 250×4 mm.
Column temperature: 50° C.
Mobile Phase: A water+5% $CH_3CN$; C $CH_3CN$; D 0.03M potassium phosphate buffer pH 3+10% $CH_3CN$.
Gradient (t[min], A:C:D): (0, 85:0:15); (8, 15:70:15); (19, 15:70:15); (19.5, 85:0:15).
Flow: 1.2 ml/min.
Detection: UV 225 nm.

EXAMPLE 1 a) Preparation of (Z)-(2-Aminothiazol-4-yl)-trityloxyiminoacetic acid diethoxythiophosphoryl ester

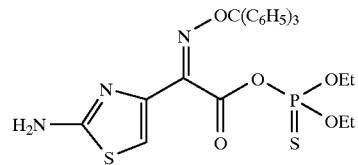

To a stirred suspension of 50 g (Z)-(2-aminothiazol4-yl)-trityloxyiminoacetic acid (116.4 mmol) and 130 mg 1,4-diazabicyclo[2.2.2]octane (DABCO) (1.164 mmol) in 500 ml dichloromethane was added under argon atmosphere 36 ml tributylamine (151 mmol). After 5 min, the red solution was cooled to 2° C. With the aid of a syringe pump was added over 30 min 24.5 ml diethyl chlorothiophosphate (151 mmol). Stirring was continued at 2° C. for 1.5 h. After approximately 30 min, the activated ester (Z)-(2-Aminothiazol-4-yl)-trityloxyiminoacetic acid diethoxythiophosphoryl ester started to crystallize from the brown reaction mixture. The reaction was followed by HPLC. After 1 h, the starting material was consumed. To the heterogeneous reaction mixture was added dropwise over 1.5 h 750 ml water (to remove water soluble by-products) and over 40 min 500 ml n-hexane (to drive the precipitation of the product to completion). The suspension was stirred for 1 h at 2° C. and then filtered. The crystalline product was washed with 3×100 ml water and 3×100 ml n-hexane/dichloromethane 3:1 and dried to constant weight. Activated ester (Z)-(2-Aminothiazol-4-yl)-trityloxyiminoacetic acid diethoxythiophosphoryl ester was obtained as a tan solid (64.24 g, yield=94.9%, HPLC=97.5 area %, mp=146° C.) and was stored under Ar at 4° C. No further purification was necessary and the product was used as isolated for the next step.

IR (KBr) 3444, 3092, 2983, 1770, 1618, 1541, 1490, 1024, 720; $^1$H-NMR (250 MHz, $CDCl_3$) δ 1.29 (dt,$J_1$=7,$J_2$=0.8,6H); 4.19 (dq,$J_1$=8.0,$J_2$=7.0,4H); 6.01 (s,br,2H); 6.59 (s,1H); 7.26–7.34 (m,15H); $^{31}$P-NMR (100 MHz, $CDCl_3$) δ 59,05; ISP-MS 582.4 (100, [M+H]$^+$); MA calculated for $C_{28}H_{28}N_3O_5PS_2$ C 57.82, H 4.85, N 7.22, S 11.02, P 5.33; found C 58.09, H 4.96, N 7.21, S 10.92, P 5.35 and 0.35% water.

b) (6R, 7R)-7-[(Z)-2-(2-Aminothiazol-4-yl)-2-trityloxyimino-acetylamino)]-3-[(E)-1-cyclopropylmethyl-2-oxo-pyrrolidin-3-ylidenemethyl]-8-oxo-5-thia-1-azabicyclo[4.2.0]oct-2-ene-2-carboxylic acid triethylammonium salt

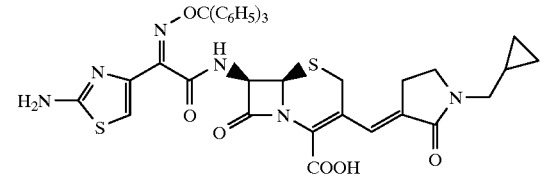

To a stirred suspension of 22.78 g (E)-(6R,7R)-7-amino-3-(1-cyclopropylmethyl-2-oxo-pyrrolidin-3-ylidenemethyl)-8-oxo-5-thia-1-azabicyclo[4.2.0]oct-2-ene-2-carboxylic acid (65.2 mmol) in 160 ml dimethylformamide was added under argon 9.1 ml triethylamine (65.2 mmol) at 10° C. After 30 min, to the solution was added 48 ml 2-propanol and 3.9 ml water causing the starting material to precipitate partially. The suspension was cooled to 2° C. and over 5 min was added in portions 36.68 g activated ester (Z)-(2-Aminothiazol-4-yl)-trityloxyiminoacetic acid diethoxythiophosphoryl ester (66.5 mmol). Stirring was continued at room temperature with exclusion of light for 17 h. The reaction was followed by HPLC. To the slightly turbid reaction mixture was added over 2 min 9.2 ml triethylamine (65.2 mmol, 1.0 eq) resulting in a clear, yellow solution. Reference material was added and after ca. 15 min, the reaction mixture became turbid, indicating the onset of crystallization. Stirring at room temperature was continued for 60 min and then 330 ml ethylacetate was added dropwise over 90 min. To drive crystallization to completion the suspension was cooled to 2° C. and stirred for 3 h at this temperature. The suspension was filtered. The crystalline product was washed with 3×100 ml ice-cold ethylacetate and dried to constant weight. The cephalosporin (6R, 7R)-7-[(Z)-2-(2-Aminothiazol-4-yl)-2-trityloxyimino-acetylamino)]-3-[(E)-1-cyclopropylmethyl-2-oxo-pyrrolidin-3-ylidenemethyl]-8-oxo-5-thia-1-aza-bicyclo[4.2.0]oct-2-ene-2-carboxylic acid triethylammonium salt was obtained as an off-white solid (51.56 g, yield=77%, HPLC=100 area %) and was stored under Ar at 4° C. No further purification was necessary and the product was used as isolated for the next step.
Anal.
$^1$H-NMR (250 MHz, DMSO) δ 0.20 (m,2H); 0.46 (m,2H); 0.92 (m,1H); 3.14 (d,J=7.0,2H); 3.22–4.09 (mm, 7H); 3.78, 3.82 (2d,J=16.0,2H); 5.16 (d,J=5.0,1H); 5.87 (dd,$J_1$=13.2,$J_2$=8.3,1H); 6.61 (s,1H); 7.23–7.33 (mm,16H); 9.90 (d,J=8.3,1H)+signals for NEt$_3$ and DMF; calculated for $C_{40}H_{36}N_6O_6S_2:C_6H_{15}N:C_3H_7NO$=1:1:2 and 0.36% H$_2$O C 61.94, H 6.50, N 12.50, S 6.36; found C 61.49, H 6.29, N 12.17, S 6.69.

EXAMPLE 2
a) Preparation of (Z)-(2-Aminothiazol-4-yl)-acetoxyiminoacetic acid diethoxythiophosphoryl ester

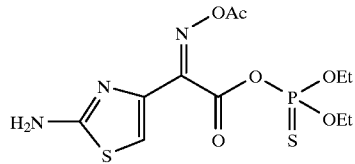

To a stirred solution of 134.9 g (Z)-(2-aminothiazol4-yl)-acetoxyiminoacetic acid dihydrate (508.6 mmol) and 570 mg 1,4-diazabicyclo[2.2.2]octane (DABCO) (5.09 mmol) in 1500 ml dimethylacetamide was added under argon 158 ml tributylamine (661 mmol). The yellowish solution was cooled to −20° C. and over 30 min was added dropwise 104 ml diethyl chlorothiophosphate (661 mmol). Stirring was continued at −20° C. for 3.5 h. The reaction was followed by HPLC. After 3 h, all starting material was consumed. The reaction mixture was allowed to warm up to 0° C. and over 1.0 h was added dropwise 2200 ml water. The precipitated product was filtered, washed with water and dissolved in 800 ml dichloromethane. The aqueous layer was back-extracted with 300 ml dichloromethane. The combined organic layers were dried over 70 g sodium sulfate and concentrated under reduced pressure until the product started to crystallize. The residual solution was cooled to 2° C. and 1200 ml n-hexane was added dropwise over 1 h. The resulting suspension was stirred for 1 h at 2° C. and then filtered. The crystalline product was washed with n-hexane and dried to constant weight. (Z)-(2-aminothiazol-4-yl)-acetoxyiminoacetic acid diethoxythiophosphoryl ester was obtained as a white solid (166.9 g, yield=86%, mp 128–130° C. and was stored under argon at −20° C. No further purification was necessary and the product was used as isolated for the next step.
IR (KBr) 3429, 3260, 3172, 3135, 1795, 1770, 1619, 1538, 1174, 1020; $^1$H-NMR (250 MHz, CDCl$_3$) δ 1.38 (dt,$J_1$=7.0,$J_2$=0.9,6H); 2.26 (s,3H); 4.34 (dq,$J_1$=8.0,$J_2$=7.0, 4H); 6.94 (s,1H); 7.50 (s,br,2H); $^{31}$P-NMR (100 MHz, CDCl$_3$) δ 59.27; ISP-MS 404.1 (31, [M+Na]$^+$), 382.1 (100, [M+H]$^+$); MA calculated for $C_{11}H_{16}O_6N_3PS_2$, C 34.64, H 4.23, N 11.02, S 16.81, P 8.12; found C 34.64, H 4.18, N 11.07, S 16.67, P 8.02.
b) Preparation of (6R,7R)-7-[(Z)-2-(2-aminothiazol-4-yl)-2-acetoxyimino-acetylamino)]-3-[(E)-1-cyclopropylmethyl-2-oxo-pyrrolidin-3-ylidenemethyl]-8-oxo-5-thia-1-azabicyclo [4.2.0]oct-2-ene-2-carboxylic acid

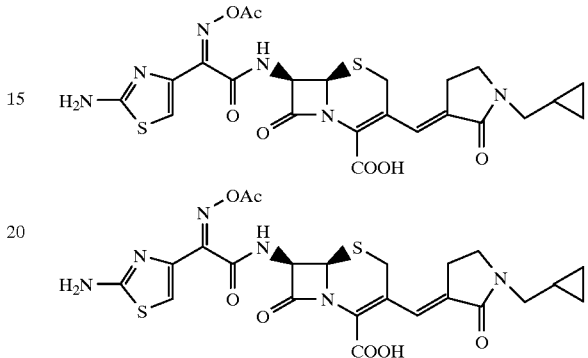

Under an argon atmosphere to a stirred suspension of 25.6 g (E)-(6R,7R)-7-Amino-3-(1-cyclopropylmethyl-2-oxo-pyrrolidin-3-ylidenemethyl)-8-oxo-5-thia-1-azabicyclo [4.2.0]oct-2-ene-2-carboxylic acid (73.3 mmol) in 120 ml dimethylformamide was added 20 ml triethylamine (143 mmol) at 10° C. After 15 min, the solution was cooled to 0° C. and 28.5 g (Z)-(2-aminothiazol-4-yl)-acetoxyiminoacetic acid diethoxy thiophosphonyl ester (74.8 mmol) was added in portions over 5 min. Stirring was continued at 0° C. with exclusion of light for 5 h. The reaction was followed by HPLC. The brown reaction mixture was poured at once into 550 ml water of 10° C. Over 30 min, 50 ml HCl 1N was added. The pH dropped from 4.6 to 3.2 and the product precipitated from the reaction mixture. Stirring was continued for 1 h at 0° C. The suspension was filtered. The product was washed with ice-cold water, re-suspended in water, stirred for 20 min at room temperature, filtered and again washed with water. (6R,7R)-7-[(Z)-2-(2-aminothiazol-4-yl)-2-acetoxyimino-acetylamino)]-3-[(E)-1-cyclopropylmethyl-2-oxo-pyrrolidin-3-ylidenemethyl]-8-oxo-5-thia-1-azabicyclo[4.2.0]oct-2-ene-2-carboxylic acid was obtained as a beige, wet solid. The product was used immediately and without drying for the next step.

EXAMPLE 3
a) Preparation of (Z)-(RS)-(2-aminothiazol-4-yl)-[(tetrahydropyran-2-yloxyimino)]-acetic acid diethoxythiophosphoryl ester

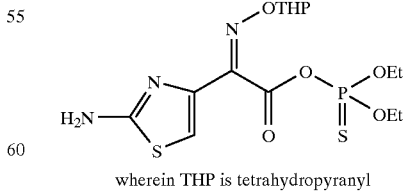

wherein THP is tetrahydropyranyl

To a stirred suspension of 30 g (Z)-(RS)-(2-aminothiazol-4-yl)-[(tetrahydropyran-2-yloxyimino)]-acetic acid (80.5 mmol) and 90 mg 1,4-diazabicyclo[2.2.2]octane (DABCO) (0.80 mmol) in 300 ml dimethylacetamide was added under argon over 45 min 17 ml diethyl chlorothiophosphate (104.9 mmol). Stirring was continued at 0° C. for 1 h. The reaction was followed by HPLC. To the slightly turbid reaction mixture was added dropwise over 50 min 450 ml water. The precipitated product was filtered, washed with water and dissolved in dichloromethane. The aqueous layer was back-extracted with dichloromethane. The combined organic layers were dried over sodium sulfate and concentrated under reduced pressure until the product started to crystallize. To the residual solution was added dropwise over 30 min n-hexane. The resulting suspension was cooled to 2° C., stirred for 1 h and then filtered. The crystalline product was washed with n-hexane and dried to constant weight. (Z)-(RS)-(2-aminothiazol-4-yl)-[(tetrahydropyran-2-yloxyimino)]-acetic acid diethoxythio-phosphoryl ester was obtained as a white solid (28.01 g, yield=82%) and was stored under argon at −20° C. No further purificiation was necessary and the product was used as isolated for the next step.

IR (KBr) 3423, 3261, 3169, 3145, 2946, 1772, 1614, 1541. 1388, 1241, 1204, 1156, 1110, 1020, 973, 944, 908, 888, 857, 827, 727, 692; $^1$H-NMR (250 MHz, CDCl$_3$) δ 1.37 (t,J=7.1,6H); 1.50–1.95 (m,6H); 3.65 (dm,J=11.4,1H); 3.86 (tm,J=11.4,1H); 4.33 (dq,J$_1$=8.0,J$_2$=7.0,4H); 5.47 (s,br,1H); 6.56 (s,br,2H); 6.79 (s,1H); $^{31}$P-NMR (100 MHz, CDCl$_3$) δ 59.33; ISP-MS 446.4 (19, [M+Na]$^+$), 424.5 (26, [M+H]$^+$), 340.2 (100); MA calculated for C$_{14}$H$_{22}$N$_3$O$_6$PS$_2$, C 39.71, H 5.24, N 9.92, S 15.14, P 7.31; found C 39.87, H 5.20, N 10.08, S 14.99, P 7.53.

b) (6R,7R)-7-[(Z)-2-(2-Aminothiazol-4-yl)-2-[(R,S)-tetrahydropyran-2-yloxyiminoacetylamino)]-3-[(E)-1-cyclopropylmethyl-2-oxo-pyrrolidin-3-ylidenemethyl]-8-oxo-5-thia-1-aza-bicyclo[4.2.0]oct-2-ene-2-carboxylic acid

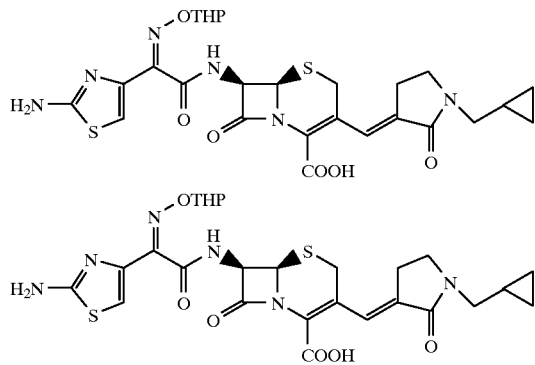

Under argon atmosphere to a stirred suspension of 20 g (E)-(6R,7R)-7-Amino-3-(1-cyclopropylmethyl-2-oxo-pyrrolidin-3-ylidenemethyl)-8-oxo-5-thia-1-azabicyclo[4.2.0]oct-2-ene-2-carboxylic acid (57.2 mmol) in 140 ml dimethylformamide was added 16 ml triethylamine (114.8 mmol) at 10° C. After 10 min, to the solution was cooled to 0° C. and 24.72 g (Z)-(RS)-(2-arinothiazol-4-yl)-[(tetrahydropyran-2-yloxyinino)]-acetic acid diethoxythiophosphoryl ester (58.4 mmol) was added in portions over 1 min. Stirring was continued at 10° C. with the exclusion of light for 6 h. The reaction was followed by HPLC. The reaction mixture was poured at once into a 10° C. mixture of 220 ml water and 50 ml acetone. Over 30 min. 55 ml HCl 1N was added. The pH dropped from 9.6 to 3.2 and the product precipitated from the reaction mixture. Stirring was continued for 30 min at 0° C. The suspension was filtered. The product was washed with ice-cold water and dried to constant weight. (6R,7R)-7-[(Z)-2-(2-Aminothiazol-4-yl)-2-[(R,S)-tetrahydropyran-2-yloxyimino-acetylamino)]-3-[(E)-1-cyclopropylmethyl-2-oxo-pyrrolidin-3-ylidenemethyl]-8-oxo-5-thia-1-aza-bicyclo[4.2.0]oct t- 2-ene-2-carboxylic acid was obtained as an off-white solid (27.7 g). The product was used as isolated for the next step.

$^1$H-NMR (250 MHz, DMSO) δ 0.21 (m,2H); 0.46 (m,2H); 0.93 (m,1H); 1.40–1.90 (m,6H); 2.90–3.10 (m,2H); 3.16 (d,J=7.1,2H); 3.48 (m,2H); 3.50 (m,1H); 3.85 (m,1H); 3.90 (s,2H); 5.21 (d,J=5.0,1H): 5.26 (s,br,1H): 5.90 (dd,J$_1$=8.2,J$_2$=5.0, 1H); 6.75 (s,1H); 7.23 (s,br,3H); 9.69 (d,J=8.2, 1H); 13.95 (s,br,1H).

EXAMPLE 4

Cleavage of the Protective Groups:

Preparation of (6R,7R)-7-[(Z)-2-(2-aminothiazol-4-yl)-2-hydroxyimino-acetylamino]-3-[(E)-1-cyclopropylmethyl-2-oxo-pyrrolidin-3-ylidenemethyl]-8-oxo-5-thia-1-aza-bicyclo[4.2.0]oct-2-ene-2-carboxylic acid

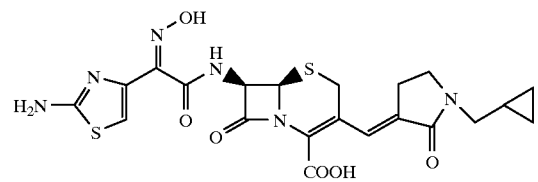

a) By cleavage of the trityl group

To a stirred solution of 30 g (6R, 7R)-7-[(Z)-2-(2-Aminothiazol-4-yl)-2-trityloxyiminoacetylamino)]-3-[(E)-1-cyclopropylmethyl-2-oxo-pyrrolidin-3-ylidenemethyl]-8-oxo-5-thia-1-aza-bicyclo[4.2.0]oct-2-ene-2-carboxylic acid triethylanimonium salt (29.2 mmol) in 60 ml dichloromethane was added over 15 min 7.5 ml triethylsilane (45.9 mmol) and over 90 min 23.9 ml trifluoroacetic acid (306 mmol) at 2° C. Stirring was continued at 10° C. for 2 h. The reaction was followed by HPLC. To the reaction mixture was added over 90 min 300 ml diethylether, causing the product to precipitate. Stirring was continued for 1 h at room temperature. The suspension was filtered. The product was washed with 2×60 ml diethylether, again suspended in 100 ml diethylether, stirred for 15 min, filtered, washed with 2×40 ml diethylether and dried to constant weight. The trifluoroacetate of (6R,7R)-7-[(Z)-2-(2-aminothiazol-4-yl)-2-hydroxyimino-acetylamino]-3-[(E)-1-cyclopropylmethyl-2-oxo-pyrrolidin-3-ylidenemethyl]-8-oxo-5-thia-1-aza-bicyclo[4.2.0]oct-2-ene-2-carboxylic acid was obtained as an off-white solid (19.92 g, 99%, HPLC=100 area %) and suspended in 400 ml water. Over 15 min 20 ml NaOH 1N (20 mmol) were added at 2° C. The pH rose from 1.51 to 3.30. The suspension was stirred at 2° C. for 10 min and then filtered. For the filtration a mild vacuum of about 400 mbar was applied. The product was washed with 2×50 ml water, suspended in 250 ml water, stirred for 15 min at 2° C., filtered, washed with 2×50 ml water and re-suspended in 400 ml water. Over 40 min 30 ml NaOH 1N was added at 2° C. The pH rose from 2.38 to 5.6 and most of the product dissolved. The turbid solution was filtered and two membrane filters of 0.45 μm and 0.22 μm. To the resulting, clear solution was added over 20 min 26 ml HCl 1N (26 mmol) at 2° C. The pH dropped from 5.42 to 3.30 and the product precipitated. The suspension was stirred for 60 min at 2° C., filtered and washed with 100 ml water. The product was dried (15 mbar, 24 h, 35° C.) to constant weight. (6R,7R)-7-[(Z)-2-(2-Aminothiazol-4-yl)-2-hydroxyimino-acetylamino]-3-[(E)-1-cyclopropylmethyl-2-oxo-pyrrolidin-3-ylidenemethyl]-8-oxo-5-thia-1-aza-bicyclo

[4.2.0]oct-2-ene-2-carboxylic acid was isolated as an off white solid (12.1 g, yield 81%, HPLC 94 area %).

$^1$H-NMR (250 MHz, DMSO) δ 0.21 (m,2H), 0.46 (m,2H); 0.93 (m,1H); 2.90 (m,1H); 3.10 (m,1H); 3.15 (d,J=7.0,2H); 3.48 (t,J=6.0,2H); 3.88 (s,2H); 5.18 (d,J=4.9,1H); 5.82 (dd,J$_1$=8.7,J$_2$=4.9,1H); 6.66 (s,1H); 7.14 (s,br,2H); 7.22 (s,1H); 9.51 (d,J=8.7,1H); 11.33 (s,br,1H).
Anal.

calculated for $C_{21}$, $H_{22}$, $N_6O_6S_2$: C 48.64, H 4.28, N 16.21, S 12.36; found C 47.88, H 4.36, N 15.85, S 12.17 and 2.47% $H_2O$.

b) By cleavage of the acetyl group

To a stirred suspension of (6R,7R)-7-[(Z)-2-(2-aminothiazol-4-yl)-2-acetoxyimino-acetylamino)]-3-[(E)-1-cyclopropylmethyl-2-oxo-pyrrolidin-3-ylidenemethyl]-8-oxo-5-thia-1-azabicyclo[4.2.0]oct-2-ene-2-carboxylic acid (used in wet form, assumed ~73.3 mmol) in 300 ml methanol was added under an argon atmosphere over 10 min 30 ml HCl conc. (304 mmol) at 2° C. After 5 h stirring at 2° C., another 10 ml HCl conc. (101 mmol) were added to the suspension. The reaction mixture was allowed to warm up to room temperature over night. The reaction was followed by HPLC. After 21 h total reaction time, all starting material was consumed and a brown solution had resulted. The reaction mixture was poured at once into 800 ml ice cold water. To the resulting suspension was added over 60 min 500 ml NaOH 1N. The pH rose from 0.6 to 3.3. Stirring at 2° C. was continued for 15 min. The suspension was filtered. The product was washed with water and dried to constant weight. (6R,7R)-7-[(Z)-2-(2-Aminothiazol-4-yl)-2-hydroxyimino-acetylamino]-3-[(E)-1-cyclopropylmethyl-2-oxo-pyrrolidin-3-ylidenemethyl]-8-oxo-5-thia-1-aza-bicyclo[4.2.0]oct-2-ene-carboxylic acid was obtained as a yellowish solid (29.8 g, yield 78%, HPLC 90 area %).

c) By cleavage of the tetrahydropyranyl (THP) group

To a stirred suspension of 20 g, (6R,7R)-7-[(Z)-2-(2-aminothiazol-4-yl)-2-[(R,S)-tetrahydropyran-2-yloxyimino-acetylamino)]-3-[(E)-1-cyclopropylmethyl-2-oxo-pyrrolidin-3-ylidenemethyl]-8-oxo-5-thia-1-aza-bicyclo[4.2.0]oct-2-ene-2-carboxylic acid (33.3 mmol) in 150 ml methanol was added over 10 min 15 ml HCl conc. (180 mmol) at room temperature. The yellow solution was stirred at 45° C. for 4.5 h. The reaction was followed by HPLC. After 4 h all starting material was consumed. The reaction mixture was allowed to cool to room temperature and poured at once into 500 ml water. To the solution was added over 40 min 170 ml NaOH 1N. The pH rose from 0.43 to 3.1. The resulting suspension was cooled to 2° C., stirred for 1 h and filtered. The product was washed with ice cold water and dried to constant weight. (6R,7R)-7-[(Z)-2-(2-aminothiazol-4-yl)-2-hydroxyimino-acetylamino]-3-[(E)-1-cyclopropylmethyl-2-oxo-pyrrolidin-3-ylidenemethyl]-8-oxo-5-thia-1-aza-bicyclo[4.2.0]oct-2-ene-2-carboxylic acid was obtained as a yellowish solid (12.8 g, yield 74%, HPLC 85 area %).

What is claimed is:

1. A compound of formula

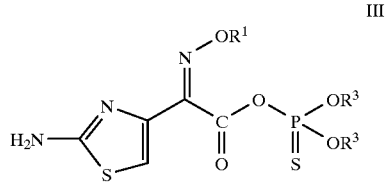

wherein $R^1$ is trityl, acetyl, tetrahydropyranyl or cyclopentyl and $R^3$ is lower alkyl.

2. The compound of claim 1 wherein $R^1$ is trityl and $R^3$ is ethyl.

3. The compound of claim 1 wherein $R^1$ is acetyl and $R^3$ is ethyl.

4. The compound of claim 1 wherein $R^1$ is tetrahydropyranyl and $R^3$ is ethyl.

* * * * *

UNITED STATES PATENT AND TRADEMARK OFFICE
CERTIFICATE OF CORRECTION

PATENT NO. : 5,919,939
DATED : July 6, 1999
INVENTOR(S) : Oberhauser

It is certified that error appears in the above-identified patent and that said Letters Patent is hereby corrected as shown below:

COVER PAGE:

The priority data should read--

"[30]   Foreign Application Priority Data   Europe   96109239.2   June 10, 1996".
--.

Signed and Sealed this

Thirtieth Day of November, 1999

Attest:

Q. TODD DICKINSON

*Attesting Officer*    *Acting Commissioner of Patents and Trademarks*